(12) United States Patent
Lee et al.

(10) Patent No.: US 9,770,674 B2
(45) Date of Patent: Sep. 26, 2017

(54) PURIFICATION DEVICE AND PURIFICATION METHOD USING THE SAME

(71) Applicant: LG CHEM, LTD., Seoul (KR)

(72) Inventors: Sung Kyu Lee, Daejeon (KR); Joon Ho Shin, Daejeon (KR)

(73) Assignee: LG CHEM. LTD., Seoul (KR)

( * ) Notice: Subject to any disclaimer, the term of this patent is extended or adjusted under 35 U.S.C. 154(b) by 29 days.

(21) Appl. No.: 14/783,715

(22) PCT Filed: Aug. 1, 2014

(86) PCT No.: PCT/KR2014/007097
§ 371 (c)(1),
(2) Date: Oct. 9, 2015

(87) PCT Pub. No.: WO2015/016653
PCT Pub. Date: Feb. 5, 2015

(65) Prior Publication Data
US 2016/0082363 A1    Mar. 24, 2016

(30) Foreign Application Priority Data

Aug. 1, 2013  (KR) .................. 10-2013-0091797
Aug. 1, 2014  (KR) .................. 10-2014-0098792

(51) Int. Cl.
*C07C 9/15*   (2006.01)
*B01D 3/14*   (2006.01)
*B01D 3/00*   (2006.01)
*C07C 7/04*   (2006.01)
*C07C 7/00*   (2006.01)
(Continued)

(52) U.S. Cl.
CPC ............. *B01D 3/007* (2013.01); *B01D 3/143* (2013.01); *B01D 3/322* (2013.01); *B01D 3/4205* (2013.01); *C07C 7/005* (2013.01); *C07C 7/04* (2013.01); *C07C 9/15* (2013.01); *Y02P 20/124* (2015.11); *Y02P 20/57* (2015.11)

(58) Field of Classification Search
CPC ........ B01D 3/007; B01D 3/143; B01D 3/322; B01D 3/4205; C07C 7/005; C07C 7/04; C07C 9/14
See application file for complete search history.

(56) References Cited

U.S. PATENT DOCUMENTS 4,256,541 A * 3/1981 Muller .................. C07C 29/80
                                                          203/19
4,277,268 A * 7/1981 Spangler, Jr. ........ B01D 1/2856
                                                          203/24
(Continued)

FOREIGN PATENT DOCUMENTS

JP    2003-503307 A    1/2003
KR    10-0442501 B1    7/2004
KR    10-2008-0089961 A    10/2008

*Primary Examiner* — Jonathan Miller
(74) *Attorney, Agent, or Firm* — Dentons US LLP (57) ABSTRACT

Provided are a purification device and method. The purification device and method make most use of an internal heat source in the distillation column in the process of distilling the raw material, and reduce use of an external heat source. Thereby, the purification device and method can improve energy efficiency of all the processes.

8 Claims, 4 Drawing Sheets

(51) Int. Cl.
*B01D 3/32* (2006.01)
*B01D 3/42* (2006.01)

(56) References Cited

U.S. PATENT DOCUMENTS

| | | | | |
|---|---|---|---|---|
| 4,428,201 | A * | 1/1984 | Carson | B01D 3/007 |
| | | | | 203/DIG. 20 |
| 4,586,986 | A * | 5/1986 | Preusser | C07C 7/005 |
| | | | | 203/22 |
| 4,615,769 | A * | 10/1986 | Horigome | C07C 7/04 |
| | | | | 202/182 |
| 4,897,098 | A * | 1/1990 | Pate | C07C 7/04 |
| | | | | 62/630 |
| 4,961,826 | A * | 10/1990 | Grethlein | B01D 1/2856 |
| | | | | 202/154 |
| 5,035,776 | A | 7/1991 | Knapp et al. | |
| 5,252,187 | A * | 10/1993 | Ohtsu | B01D 1/26 |
| | | | | 159/24.2 |
| 7,288,692 | B2 * | 10/2007 | Kuechler | C07C 1/20 |
| | | | | 585/638 |
| 7,361,799 | B2 * | 4/2008 | Kuechler | C07C 1/20 |
| | | | | 585/638 |
| 8,246,791 | B2 * | 8/2012 | McGinnis | B01D 3/146 |
| | | | | 202/153 |
| 8,840,762 | B2 * | 9/2014 | Werba | B01D 3/007 |
| | | | | 202/154 |
| 2010/0051441 | A1 | 3/2010 | Vane et al. | |
| 2013/0037404 | A1 | 2/2013 | Abdelghani | |

* cited by examiner

--PRIOR ART--

PURIFICATION DEVICE AND PURIFICATION METHOD USING THE SAME

RELATED APPLICATIONS

This application is a National Stage Entry of International Application No. PCT/KR2014/007097, filed Aug. 1, 2014, and claims the benefit of and priority to Korean Application No. 10-2013-0091797, filed Aug. 1, 2013 and Korean Application No. 10-2014-0098792, filed Aug. 1, 2014, all of which are incorporated by reference in their entirety for all purposes as if fully set forth herein.

TECHNICAL FIELD

The present invention relates to an device and method for distilling and purifying raw materials.

BACKGROUND ART

Typically, various raw materials such as crude oil are largely mixtures of numerous chemical materials, are rarely used in the industries per se, and are usually used after being separated into each compound. A representative of chemical processes of separating the mixture is a distillation process.

It is a problem to be solved in the distillation process that is to improve separation efficiency with minimum energy.

DISCLOSURE

Technical Problem

Accordingly, an object of the present invention is to provide an device and method for distilling and purifying raw materials, capable of maximizing use of internal heat source in a distillation column to reduce use of external energy.

TECHNICAL SOLUTION

Figure 1:
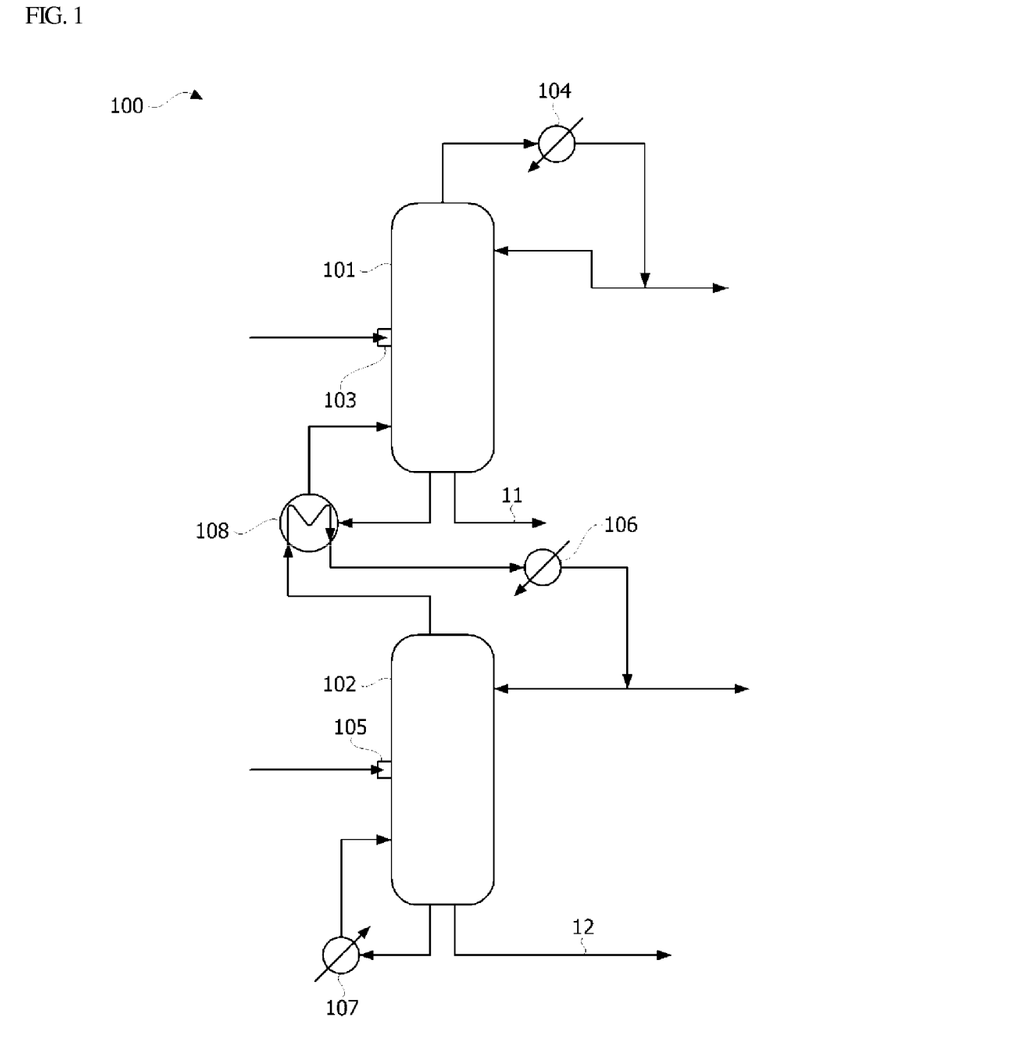
FIGS. 1 to 3 illustrate purification devices according to embodiments of the present invention.

The present invention is directed to a purification device. In one embodiment, the purification device includes a first distillation section, a second distillation section, and a heat exchanger. FIG. 1 illustrates an exemplary purification device 100. As illustrated FIG. 1, the first distillation section of the purification device 100 of the present invention includes a first distillation column 101 that has a first raw material feed port 103 into which a raw material is introduced and that distills the introduced raw material, a first condenser 104 that condenses a top stream discharged from a top section of the first distillation column 101 and returns a part of the top stream to the first distillation column, and a first discharge route 11 that conveys a material discharged from a lower section of the first distillation column 101. Further, the second distillation section of the purification device 100 of the present invention includes a second distillation column 102 that has a second raw material feed port 105 into which a raw material is introduced and that distills the introduced raw material, a second condenser 106 that condenses a top stream discharged from a top section of the second distillation column 102 and returns a part of the top stream to the second distillation column 102, a second reboiler 107 that heats a bottom stream discharged from a bottom section of the second distillation column 102 and returns a part of the bottom stream to the second distillation column 102, and a second discharge route 12 that conveys a material discharged from the bottom of the second distillation column 102. Further, the heat exchanger 108 of the purification device 100 of the present invention exchanges heat between the top stream discharged from the top section of the second distillation column 102 and a bottom stream discharged from a bottom section of the first distillation column 101 before the top stream discharged from the top section of the second distillation column 102 is introduced into the second condenser 106. Here, at least part or all of the bottom stream discharged from the bottom section of the first distillation column 101 may be returned to the bottom section of the first distillation column 101. In the present invention, the heat exchanger 108 may transfer heat from the high-temperature top stream discharged from the top section of the second distillation column 102 to the bottom stream discharged from the bottom section of the first distillation column 101. The top stream of the second distillation column 102 which flows through the heat exchanger 108 may be discharged to the second condenser 106. With the use of the heat exchanger 108, the top stream of the second distillation column 102 can be discharged to the second condenser 106 at a lower temperature, and the bottom stream of the first distillation column 101 can be heated to flow back to the first distillation column 101.

Figure 2:
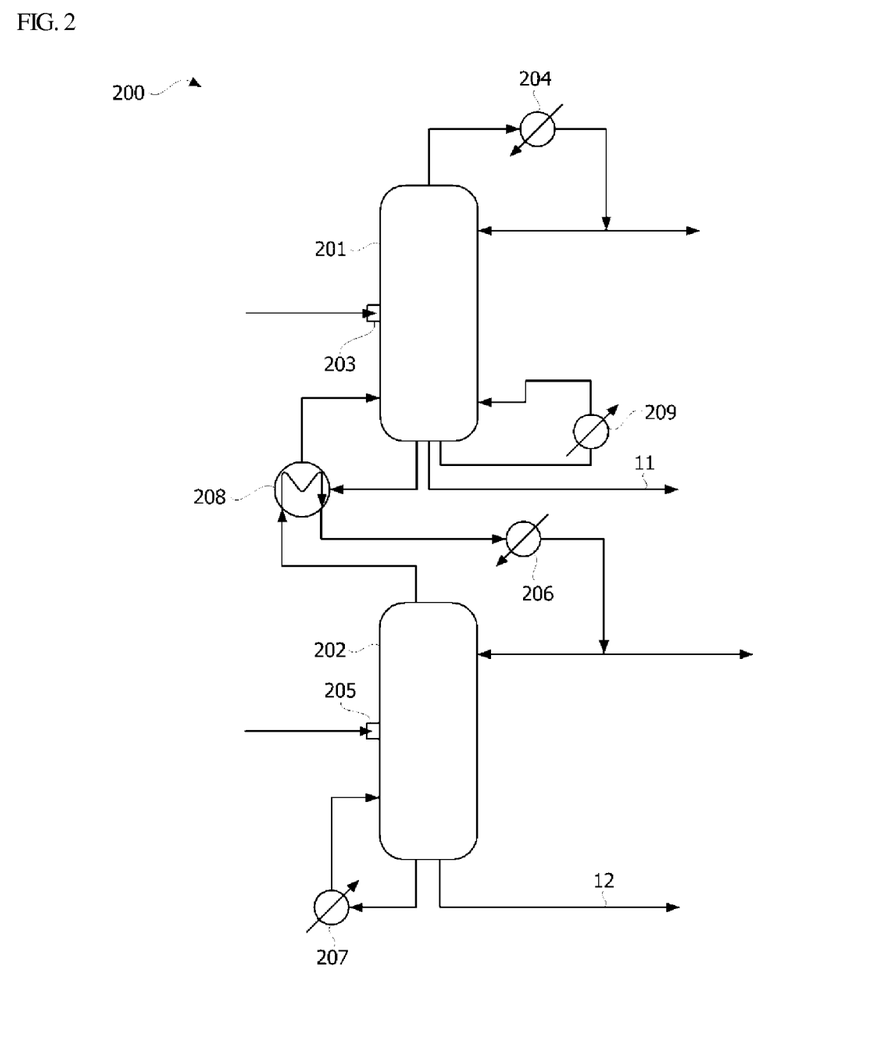

As illustrated in FIG. 2, an exemplary purification device 200 of the present invention may further include a first reboiler 209 that heats a bottom stream discharged from a bottom section of a first distillation column 201 and returns a part of the bottom stream to the first distillation column 201. The first reboiler 209 can, as in FIG. 2, heat another (second) bottom stream of the first distillation column 201 other than the bottom stream of the first distillation column 201 which flows through the heat exchanger (first bottom stream) and reflux a part of the another (second) bottom stream to the first distillation column 201, but not limited thereto. For example, although not illustrated in the figures, the first reboiler 209 may heat the bottom stream of the first distillation column 201 which flows through the heat exchanger and reflux at least part of the bottom stream. The bottom stream flowing through the first reboiler 209 may flow back to the first distillation column 201. Accordingly, the bottom stream of the first distillation column 201 is heated by a heat source transferred from a heat exchanger 208. Thereby, energy used to heat the bottom stream in the first reboiler 209 can be reduced.

In one embodiment, a operating pressure P2 of the second distillation column 102 of the present invention may be controlled to be higher than a operating pressure P1 of the first distillation column 101. For example, a difference between the operating pressure P2 of the second distillation column and the operating pressure P1 of the first distillation column may range from 0.25 to 3.5 kg/cm²g, from 1 to 3.3 kg/cm²g, from 1.5 to 3.0 kg/cm²g, or from 2.0 to 2.8 kg/cm²g. In one embodiment, a ratio P1/P2 of the operating pressure P1 of the first distillation column to the operating pressure P2 of the second distillation column may range from 0.02 to 0.85, from 0.03 to 0.80, from 0.05 to 0.73, from 0.08 to 0.70, from 0.10 to 0.67, from 0.1 to 0.65, from 0.1 to 0.60, or from 0.1 to 0.55. By controlling the pressures of the first and second distillation columns 101 and 102 as described above, a temperature of the bottom stream of the first distillation column and a temperature of the top stream of the second distillation column can be controlled as described below, and thus internal energy can be effectively used.

To exchange heat between the top stream of the second distillation column 102 and the bottom stream of the first distillation column 101, a process can be controlled in such a manner that a temperature difference generated between the top stream and the bottom stream ranges from 5° C. to 25° C., form 10° C. to 23° C., from 15° C. to 22° C., or from 18° C. to 22° C. To be specific, a ratio T1/T2 of the temperature T1 of the bottom stream of the first distillation column to the temperature T2 of the top stream of the second distillation column may range from 0.5 to 0.96, from 0.53 to 0.95, from 0.55 to 0.94, from 0.57 to 0.93, from 0.60 to 0.92, from 0.65 to 0.90, from 0.70 to 0.90, or from 0.75 to 0.85. Such a temperature ratio can be met by carrying out, but not limited to, a method of controlling the pressure of the first or second distillation column as described above.

In one embodiment, the operating pressure of the second distillation column may range from 1.5 to 3.5 kg/cm$^2$g, from 2.0 to 3.3 kg/cm$^2$g, from 2.3 to 3.0 kg/cm$^2$g, or from 2.5 to 2.9 kg/cm$^2$g. Further, the operating pressure of the first distillation column may range from 0.1 to 1.5 kg/cm$^2$g, from 0.15 to 1.0 kg/cm$^2$g, or from 0.2 to 0.8 kg/cm$^2$g. In the present invention, unless otherwise defined herein, the operating pressure is the operating pressure of the top section of the distillation column. The operating pressure is not particularly limited as long as it meets the ratio P1/P2 of the operating pressure P1 of the first distillation column to the operating pressure P2 of the second distillation column. In the present invention, the heat between the streams is exchanged under the control of the operating pressure, and the energy efficiency of the processes can be improved by heat exchange between existing processes instead of an external heat source.

Figure 3:
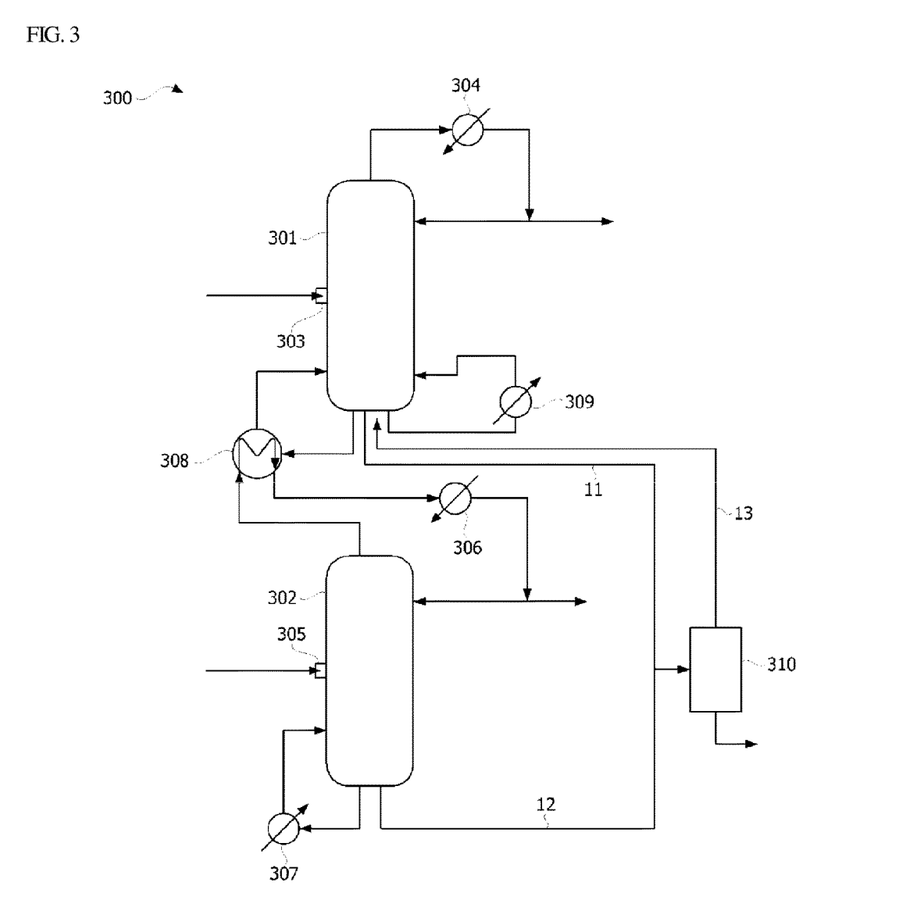

Further, in another embodiment, as illustrated in FIG. 3, a purification device 300 of the present invention may further include a recovery unit 310 that recovers a material discharged from a first discharge route 11 or a second discharge route 12. The recovery unit 310 may recover some effective components from the material discharged from at least one of the first discharge route 11 and the second discharge route 12.

Meanwhile, as a plan for the heat exchange between the bottom stream of the first distillation column 101 and the top stream of the second distillation column 102, in addition to adjusting the pressure, a part of the top product of the first distillation column 101 may be discharged to the bottom stream of the first distillation column 101. The high-temperature bottom stream of the lower section of the first distillation column 101 is mixed with a part of the low-temperature top product of the first distillation column. Thereby, a concentration of a material having a high boiling point in the bottom stream is relatively reduced, and a temperature of the entire bottom stream of the first distillation column 101 is reduced. In a relation between the bottom stream of the first distillation column 101 and the top stream of the second distillation column 102, the aforementioned temperature ratio T1/T2 can be satisfied. The method of discharging the top product of the first distillation column 101 to the bottom stream of the first distillation column 101 is not particularly limited, and may be performed using the typical process of the related art. In one embodiment, a flow rate is controlled using the first discharge route 11 of the first distillation column 101 as described below, and thereby the top product of the first distillation column can be discharged to the bottom stream or the lower-section discharge material flowing to the first discharge route 11, but the embodiment is not limited thereto.

The term "top product" used herein refers to a material rich in low-boiling-point components that are produced in the top section of the first or second distillation column and have a relatively low boiling point, whereas the term "bottom product" used herein refers to a material rich in high-boiling-point components that are produced in the bottom section of the first or second distillation column and have a relatively high boiling point. Here, the term "material rich in low-boiling-point components" refers to a material in which a content of the low-boiling-point component that is produced in the top section and has a relatively low boiling point is higher than each of contents of low-boiling-point, high-boiling-point, and medium-boiling-point components included in the raw material. For example, the material rich in low-boiling-point components may refer to a product in which the content of the low-boiling-point component included therein is equal to or more than 80% by weight, 90% by weight, 95% by weight, or 99% by weight. Further, the term "material rich in high-boiling-point components" refers to a material in which a content of the high-boiling-point component that is produced in the bottom section and has a relatively high boiling point is higher than each of contents of low-boiling-point, high-boiling-point, and medium-boiling-point components included in the raw material. For example, the material rich in high-boiling-point components may refer to a product in which the content of the low-boiling-point component included therein is equal to or more than 80% by weight, 90% by weight, 95% by weight, or 99% by weight. Further, the term "top section" used herein refers to an upper section of the first or second distillation column, and may particularly refer to an upper section of the column based on the first or second raw material feed port into which the raw material is fed. Further, the term "bottom section" used herein refers to a lower section of the first or second distillation column, and may particularly refer to a lower section of the column based on the first or second raw material feed port into which the raw material is fed.

As described above, to maximize heat exchanging efficiency if necessary, it is necessary to further reduce the temperature of the bottom stream of the first distillation column 301. In this case, a flow rate of the material discharged from the lower section through the first discharge route 11 of the first distillation column may be controlled. Here, some effective components can be additionally recovered from the discharged material using the recovery unit 310.

In specific examples of the present invention, a ratio V2/V1 of a flow rate V2 of the material flowing out of the first discharge route 11 to a flow rate V1 of the raw material flowing into the first raw material feed port may range from 0.0009 to 0.005, from 0.001 to 0.004, from 0.0015 to 0.0035, from 0.0016 to 0.0034, from 0.0017 to 0.0033, from 0.0018 to 0.0032, from 0.0019 to 0.0031, from 0.002 to 0.003, from 0.0021 to 0.0029, or from 0.0022 to 0.0028. Further, a ratio V4/V3 of a flow rate V4 of the material flowing out of the second discharge route 12 to a flow rate V3 of the raw material flowing into the second raw material feed port may range from 0.0009 to 0.004, from 0.001 to 0.003, from 0.001 to 0.0025, from 0.0011 to 0.0024, from 0.0012 to 0.0023, from 0.0013 to 0.0022, from 0.0014 to 0.0021, or from 0.0015 to 0.002. In one embodiment, in the purification device of the present invention, a value of V2/V1 may be greater than a value of V4/V3. That is, the flow rate of the material flowing out of the lower section of the first distillation column can be controlled to be greater. A ratio V6/V5 of a flow rate V6 of the material recovered by the recovery unit to a total flow rate V5 of the raw materials flowing into the first and second raw material feed ports may range from 0.001 to 0.005, from 0.0012 to 0.0045, from 0.0013 to 0.004, from 0.0014 to 0.0035, from 0.0015 to 0.003, or from 0.0016 to 0.0025. As described above, the flow rate is controlled in the purification device of the present invention which includes the first and second distillation columns. Thereby, desired internal energy can be more effectively used in the present invention. To be specific, the ratio V2/V1 of the flow rate V2 of the material flowing out of the first discharge route 11 to the flow rate V1 of the raw material flowing into the first raw material feed port is controlled, and thereby an amount of the material flowing out of the lower section of the first distillation column is controlled to be able to discharge the top product of the first distillation column to the bottom stream. Thus, it is possible to control the bottom temperature of the first distillation column as described above and to efficiently perform heat exchange. Further, the ratio V4/V3 of the flow rate V4 of the material flowing out of the second discharge route 12 to the flow rate V3 of the raw material flowing into the second raw material feed port is controlled, and thereby the top or bottom temperature of the second distillation column can be controlled as described above. In addition, the ratio V6/V5 of the flow rate V6 of the material recovered by the recovery unit to the total flow rate V5 of the raw materials flowing into the first and second raw material feed ports is controlled. Thereby, it is possible to more efficiently recover the effective material and to improve the efficiency of all the processes.

In one embodiment, the purification device of the present invention may further include a connection route 13 that delivers a vapor phase of the recovery unit 310 to the lower section of the first distillation column 301. The vapor phase of an upper section of the recovery unit 310 may be delivered to the lower section of the first distillation column 301. That is, entire energy supplied to the recovery unit may be recovered and used. In this way, the vapor phase of the recovery unit 310 is introduced into the lower section of the first distillation column 301, and thereby the recovery unit can performed the same function as the reboiler. In one embodiment, a ratio V7/V6 of a flow rate V7 of the material flowing into the lower section of the first distillation column via the connection route 13 to a flow rate V5 of the material recovered by the recovery unit may range from 0.5 to 0.95, from 0.55 to 0.93, from 0.60 to 0.90, from 0.65 to 0.89, from 0.67 to 0.88, from 0.7 to 0.87, from 0.75 to 0.86, or from 0.77 to 0.85. As described above, the flow rate of the material recovered by the recovery unit and the flow rate of the material flowing into the lower section of the first distillation column via the connection route are controlled. Thereby, energy efficiency of all the processes can be improved using a heat source of the recovery unit.

In the present invention, the raw material is not particularly limited. In one embodiment, the first and second distillation columns of the present invention may be used in, but not limited to, a solvent recovery process. The purification device of the present invention may be applied without limitation in the case of a chemical process of separating a mixture. Thus, some effective components recovered through the recovery unit 310 may be a solvent. The solvent may include, but not limited to, n-hexane.

The present invention also relates to a purification method for a raw material. The purification method may be performed using, for instance, the aforementioned purification device. The exemplary purification method may include a process of introducing a first raw material into a first distillation column 101, a process of introducing a second raw material into a second distillation column 102, a process of separating each of the introduced raw materials into top and bottom streams in each of the first and second distillation columns 101 and 102, and a process of exchanging heat between the top stream flowing out of a top section of the second distillation column 102 and the bottom stream flowing out of a bottom section of the first distillation column 101. In one embodiment, heat exchange can be caused between existing processes instead of an external heat source by exchanging the heat in the heat exchanging process. A operating pressure or temperature of at least one of the first and second distillation columns may be controlled as described above. Further, a flow rate of a stream of at least one of the first and second distillation columns may be controlled as described above.

In one embodiment, the purification method of the present invention may further include a process of recovering a material flowing out of a lower section of the first distillation column or the second distillation column. That is, the material flowing out of the lower section of each distillation column via a first discharge route 11 of the first distillation column or a second discharge route 12 of the second distillation column may be recovered by the aforementioned recovery unit. Further, the purification method may further include a process of delivering a vapor phase generated in the recovering process to the lower section of the first distillation column. That is, the vapor phase can be delivered to the lower section of the first distillation column via a connection route 13 of the recovery unit. The purification method of the present invention may recover a solvent in the recovering process.

In specific examples of the present invention, as described above, the purification method may exchange the heat based on a temperature difference between the bottom stream of the first distillation column 301 and the top stream of the second distillation column 302. In one embodiment, for the purpose of the heat exchange, as described above, the bottom stream of the first or second distillation column 301 or 302 is discharged. Thereby, temperature of the bottom stream of the first distillation column 301 and temperature of the top stream of the second distillation column 302 can be controller. For example, in the purification method of the present invention, as the process of exchanging the heat between the bottom stream of the first distillation column 101 and the top stream of the second distillation column 102, in addition to adjusting a pressure, a part of the top produce of the first distillation column 101 may be discharged to the bottom stream of the first distillation column 101.

The high-temperature bottom stream of the lower section of the first distillation column 101 is mixed with a part of the low-temperature top product of the first distillation column. Thereby, a concentration of a material having a high boiling point in the bottom stream is relatively reduced, and a temperature of the entire bottom stream of the first distillation column 101 is reduced. In a relation between the bottom stream of the first distillation column 101 and the top stream of the second distillation column 102, the aforementioned temperature ratio T1/T2 can be satisfied. The method of discharging the top product of the first distillation column 101 to the bottom stream of the first distillation column 101 is not particularly limited, and may be performed using the typical process of the related art. In one embodiment, a flow rate is controlled using the first discharge route 11 of the first distillation column 101 as described below, and thereby the top product of the first distillation column can be discharged to the bottom stream, but the embodiment is not limited thereto.

ADVANTAGEOUS EFFECTS

The purification device and method of the present invention make most use of an internal heat source in the distillation column in the process of distilling the raw material, and reduce use of an external heat source, thereby making it possible to improve energy efficiency of all the processes.

DESCRIPTION OF SYMBOLS AND NUMERALS 100, 200, 300, 400: purification device
101, 201, 301, 401: first distillation column
102, 202, 302, 402: second distillation column
103, 203, 303, 403: first raw material feed port
104, 204, 304, 404: first condenser
105, 205, 305, 405: second raw material feed port
106, 206, 306, 406: second condenser
107, 207, 307, 407: second reboiler
108, 208, 308: heat exchanger
209, 309, 409: first reboiler
310: recovery unit
11: first discharge route
12: second discharge route
13: connection route

MODE FOR INVENTION

Hereinafter, the present invention will described in greater detail based on Examples and Comparative Examples. However, the scope of the present invention is not restricted by Examples below.

Example 1

As in FIG. 1, n-hexane was recovered using the purification device. To be specific, a raw material including the n-hexane was introduced into the purification device, and a separating process was performed. Here, the first distillation column of the purification device was configured in such a manner that a operating pressure was set to about 0.3 Kg/cm²g at the top section thereof and that a operating temperature was set to about 77° C. at the top section thereof and about 95° C. at the bottom section thereof, and the second distillation column was configured in such a manner that a operating pressure was set to about 2.8 Kg/cm²g at the top section thereof and that a operating temperature was set to about 117° C. at the top section thereof and about 134° C. at the bottom section thereof. A part of the bottom stream discharged to the bottom section of the first distillation column flowed back to the first distillation column via the heat exchanger. Further, a part of the top stream of the top section of the first distillation column was re-introduced into the first distillation column via the condenser, and the other was separated into a product. Further, a part of the top stream of the top section of the second distillation column was condensed via the heat exchanger and the condenser in turn and flowed back to the second distillation column, and the other was condensed via the heat exchanger and the condenser in turn and stored as a product. Further, a part of the bottom stream discharged from the bottom section of the second distillation column flowed through the reboiler, and flowed back to the second distillation column. Further, the materials flowed out of the lower sections of the first and second distillation columns were delivered through the first and second discharge routes, respectively.

In the process, a flow rate V1 of the raw material flowing into the first raw material feed port was controlled to be 22 ton/hr, a flow rate V2 of the material discharged to the first discharge route was controlled to be 0.05 ton/hr, a flow rate V3 of the raw material flowing into the second raw material feed port was controlled to be 45 ton/hr, and a flow rate V4 of the material discharged to the second discharge route was controlled to be 0.07 ton/hr.

Example 2

As in FIG. 2, a raw material was purified in the same method as in Example 1 except that another bottom stream than a bottom stream flowing through the heat exchanger of the first distillation column was heated by the reboiler and flowed back to the first distillation column.

Example 3

As in FIG. 3, a raw material was purified in the same method as in Example 2 except that the purification device further included the recovery unit for recovering the materials discharged from the bottom sections of the first and second distillation columns and the connection route for connecting the recovery unit and the lower section of the first distillation column.

In this process, a flow rate V5 of the raw material flowing into each of the first and second raw material feed ports was controlled to be 67 ton/hr, a flow rate V6 of the material recovered by the recovery unit was controlled to be 0.12 ton/hr, and a flow rate V7 of the material flowing into the lower section of the first distillation column via the connection route was controlled to be 0.1 ton/hr.

Example 4

A raw material was purified in the same method as in Example 1 except that a flow rate of the raw material fed to the first distillation column was set to 45 ton/hr and a flow rate of the raw material fed to the second distillation column was set to 22 ton/hr. A flow rate V2 of the material flowing out of the lower section of the first distillation column via the first discharge route was 0.07 ton/hr, and a flow rate V4 of the material flowing out of the lower section of the second distillation column via the second discharge route was 0.05 ton/hr.

Comparative Example 1

Figure 4:
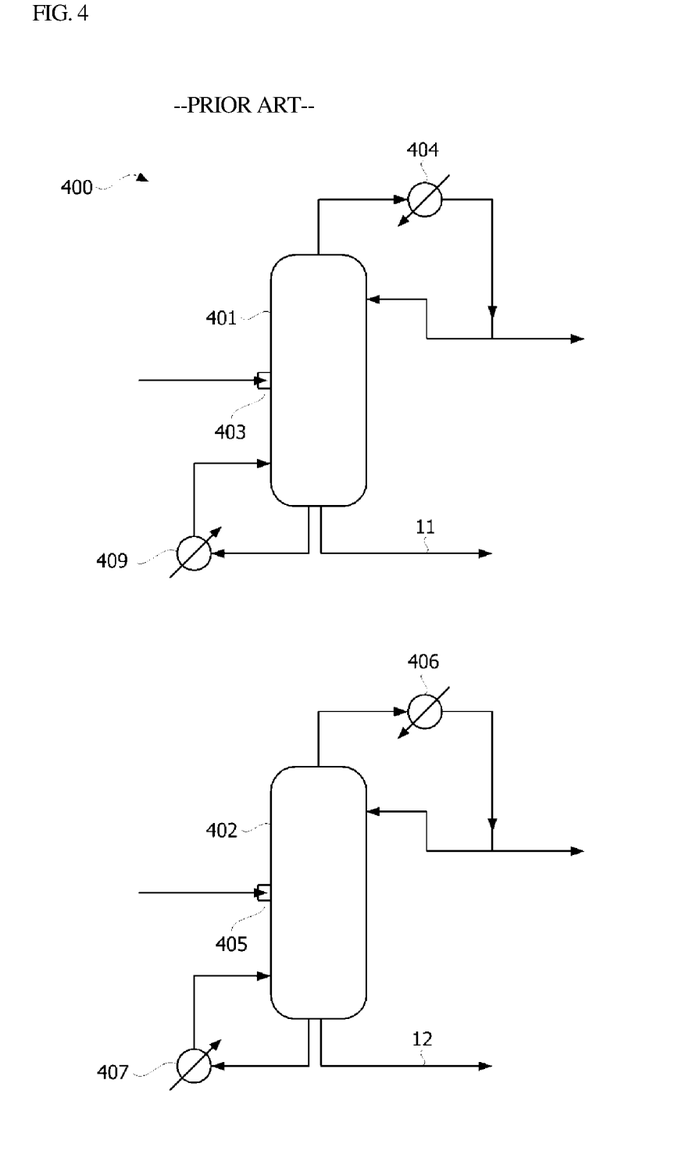
FIG. 4 illustrates a prior art purification device.

As illustrated in FIG. 4, n-hexane was recovered without cooperating with a first distillation column 401 and a second distillation column 402. A raw material was purified in the same method as Example 2, and a heat exchanger was not used. Each of the first and second distillation columns of the purification device was controlled in such a manner that a operating pressure of a top section thereof was set to about 0.75 Kg/cm²g, a operating temperature was set to about 88° C. at the top section thereof and about 115° C. at a bottom section thereof

TABLE 1

Measurement of consumed energy

|  | Example 1 | Example 2 | Example 3 | Example 4 | Comparative Example 1 |
|---|---|---|---|---|---|
| Quantity of consumed energy of first distillation column (Gcal/hr) | 2.5 | 2.5 | 2.5 | 1.3 | 2.2 |
| Quantity of consumed energy of second distillation column (Gcal/hr) | 3.1 | 3.1 | 3.0 | 4.5 | 3.4 |
| Quantity of consumed energy of recovery unit (Gcal/hr) | 0.0 | 0.0 | 0.1 | 0.0 | 0.0 |
| Quantity of recovered energy (Gcal/hr) | 2.5 | 2.0 | 2.5 | 1.3 | 0.0 |
| Total quantity of consumed energy (Gcal/hr) | 3.1 | 3.6 | 3.0 | 4.5 | 5.6 |
| Quantity of saved energy (Gcal/hr) | 2.5 | 2.0 | 2.6 | 1.1 | — |
| Rate of saved energy (%) | 44.6 | 35.7 | 46.4 | 19.6 | — |

TABLE 2

Measurement of purity of product

|  | Composition | Example 1 | Example 2 | Example 3 | Example 4 | Comparative Example 1 |
|---|---|---|---|---|---|---|
| First distillation column | Light | 1.66 | 1.66 | 1.66 | 1.66 | 1.66 |
| | n-Hexane | 98.32 | 98.32 | 98.32 | 98.32 | 98.32 |
| | Heavy | 0.02 | 0.03 | 0.02 | 0.02 | 0.02 |
| Second distillation column | Light | 0.93 | 0.93 | 0.93 | 0.93 | 0.93 |
| | n-Hexane | 99.05 | 99.05 | 99.05 | 99.05 | 99.05 |
| | Heavy | 0.02 | 0.02 | 0.02 | 0.02 | 0.02 |

It can be found from Examples and Comparative Example that Examples of the present invention can cut down the energy without a difference in purity of the product.

The invention claimed is:

1. A purification method for recovering n-hexane using a purification device,
wherein the purification device comprises a first distillation section comprising a first distillation column that has a first raw material feed port into which a raw material is introduced and that distills the introduced raw material, a first condenser that condenses a top stream discharged from a top section of the first distillation column and flows a part of the top stream back to the first distillation column, and a first discharge route that delivers a material discharged from a lower section of the first distillation column;
a second distillation section comprising a second distillation column that has a second raw material feed port into which a raw material is introduced and that distills the introduced raw material, a second condenser that condenses a top stream discharged from a top section of the second distillation column and flows a part of the top stream back to the second distillation column, a second reboiler that heats a bottom stream discharged from a bottom section of the second distillation column and flows at least a part of the bottom stream back to the second distillation column, and a second discharge route that delivers a material discharged from a lower section of the second distillation column;
a heat exchanger that exchanges heat between the top stream discharged from the top section of the second distillation column and a first bottom stream discharged from a bottom section of the first distillation column before the top stream discharged from the top section of the second distillation column is introduced into the second condenser, and
a first reboiler that heats a second bottom stream of the first distillation column other than the first bottom stream which flows through the heat exchanger, wherein the first reboiler flows at least a part of the second bottom stream back to the first distillation column, and
wherein the purification method comprises:
a process of introducing a first raw material comprising the n-hexane into the first distillation column through the first raw material feed port;
a process of introducing a second raw material comprising the n-hexane into the second distillation column through the second raw material feed port;
a process of separating each of the introduced first and second raw materials into the top and bottom streams in each of the first and second distillation columns; and
a process of exchanging heat between the top stream discharged from the top section of the second distillation column and the first bottom stream discharged from the bottom section of the first distillation column in the heat exchanger,
wherein a temperature difference generated between the top stream of the second distillation column and the first bottom stream of the first distillation column ranges from 5° C. to 25° C., and wherein a ratio (T1/T2) of a temperature (T1) of the bottom stream of the first distillation column to a temperature (T2) of the top stream of the second distillation column ranges from 0.5 to 0.96.

2. The purification method according to claim 1, wherein a ratio (P1/P2) of an operating pressure (P1) of the first distillation column to an operating pressure (P2) of the second distillation column ranges from 0.02 to 0.85.

3. The purification method according to claim 1, wherein the purification device further comprises a recovery unit that recovers a material discharged from the first discharge route or the second discharge route.

4. The purification method according to claim 1, wherein a ratio (V2/V1) of a flow rate (V2) of a material discharged from the first discharge route to a flow rate (V1) of a material introduced from the first raw material feed port ranges from 0.0009 to 0.005.

5. The purification method according to claim 1, wherein a ratio (V4/V3) of a flow rate (V4) of a material discharged from the second discharge route to a flow rate (V3) of a material introduced from the second raw material feed port ranges from 0.0009 to 0.004.

6. The purification method according to claim 3, wherein a ratio (V6/V5) of a flow rate (V6) of the material recovered by the recovery unit to a total flow rate (V5) of materials introduced from the first and second raw material feed ports ranges from 0.001 to 0.005.

7. The purification method according to claim 3, wherein the purification device further comprises a connection route that delivers a vapor phase of the recovery unit to the lower section of the first distillation column.

8. The purification method according to claim 7, wherein a ratio (V7/V6) of a flow rate (V7) of the material introduced into the lower section of the first distillation column through the connection route to a flow rate (V6) of the material recovered by the recovery unit ranges from 0.5 to 0.95.

\* \* \* \* \*